United States Patent [19]

Garg

[11] Patent Number: 5,125,262

[45] Date of Patent: Jun. 30, 1992

[54] METHOD OF DETERMINING OXYGEN DEMAND OF A LIQUID

[76] Inventor: Raj P. Garg, Thapar Institute of Engineering and Technology, Patiala-147 001, India

[21] Appl. No.: 660,135

[22] Filed: Feb. 22, 1991

Related U.S. Application Data

[63] Continuation of Ser. No. 255,746, Oct. 11, 1988, Pat. No. 5,025,927, which is a continuation-in-part of Ser. No. 130,425, Dec. 9, 1987, Pat. No. 4,783,172, which is a continuation-in-part of Ser. No. 783,632, Oct. 3, 1985, abandoned, and a continuation-in-part of Ser. No. 77,165, Jul. 24, 1987, abandoned, and a continuation-in-part of Ser. No. 783,631, Oct. 3, 1985, abandoned.

[51] Int. Cl.⁵ ............................................ G01N 33/18
[52] U.S. Cl. .................................. 73/19.12; 73/864.62; 206/527; 422/79
[58] Field of Search .......................... 73/19.12, 864.62; 206/527; 422/79

[56] References Cited

U.S. PATENT DOCUMENTS

| | | | |
|---|---|---|---|
| 2,655,011 | 10/1953 | Ihle et al. | 366/274 |
| 3,176,517 | 4/1965 | Chelminski | 73/864.62 |
| 3,242,740 | 3/1966 | Niskin | 73/864.62 |
| 3,421,528 | 1/1969 | Gomez et al. | 366/274 |
| 3,426,745 | 2/1969 | Farr | 73/864.62 |
| 3,531,995 | 10/1970 | Barker | 73/864.62 |
| 4,188,989 | 2/1980 | Anderson | 73/864.51 |
| 4,302,974 | 12/1981 | Niskin | 73/864.62 |
| 4,409,850 | 10/1983 | Zeck | 73/864.62 |
| 4,459,865 | 7/1984 | Welker | 73/864.62 |
| 4,461,186 | 7/1984 | Brannstrom et al. | 73/864.62 |
| 4,463,599 | 8/1984 | Welker | 73/864.62 |
| 4,568,195 | 12/1986 | Herz et al. | 366/274 |
| 4,783,172 | 11/1988 | Garg | 206/527 |

Primary Examiner—Hezron E. Williams
Assistant Examiner—Joseph W. Roskos
Attorney, Agent, or Firm—Browning, Bushman, Anderson & Brookhart

[57] ABSTRACT

Various embodiments of respirometers are used to determine the biochemical oxygen demand (BOD) of samples. The respirometer includes chamber walls formed from a membrane permeable to oxygen, thereby allowing reoxidation of the contained sample. In order to ensure reliability in the computed BOD values, the respirometer preferably incorporates a framed structure, and the fluid containing chamber has a predetermined volume and repeatable configuration. The present invention is particularly directed to an improved method of determining oxygen demand for respiring liquid samples, utilizing the dissolved oxygen data and the rate of oxygen transfer through the respirometer walls.

20 Claims, 4 Drawing Sheets

METHOD OF DETERMINING OXYGEN DEMAND OF A LIQUID

PRIOR RELATED APPLICATIONS

This application is a continuation of U.S. Ser. No. 07/255,746 filed on Oct. 11, 1988, now U.S. Pat. No. 5,025,927, which is a continuation-in-part of U.S. Ser. No. 07/130,425 filed on Dec. 9, 1987, now U.S. Pat. No. 4,783,172. U.S. Ser. No. 130,425 in turn is a continuation-in-part of U.S. Ser. No. 783,632 filed on Oct. 3, 1985, Ser. No. 77,165 filed on Jul. 24, 1987, and Ser. No. 783,631 filed on Oct. 3, 1985, which applications are now abandoned.

FIELD OF THE INVENTION

This invention relates to a respirometer for the determination of oxygen consumption of a respiring liquid. More specifically, this invention relates to a respirometer for testing of wastewater samples to determine its BOD. The abbreviation BOD is a standardised abbreviation in the art for the Biochemical Oxygen Demand.

BACKGROUND OF THE INVENTION

Due to limited solubility of oxygen in water, it was hitherto necessary to dilute the wastewater with specially prepared aerated dilution water and then carry out the standard BOD test in glass bottles referred to as BOD bottles. One distinct disadvantage associated with this standard BOD test procedure is that the results are not standardised, as the oxygen consumed is dependent on the extent of dilution of wastewater sample.

In the standard test procedure, wastewater, having 10 mg/l ultimate BOD, can be tested. In order to obviate such disadvantage and to determine the BOD of less dilute samples, various constructions of manometric and respirometric instrumental techniques are known in the art. In these methods, dissolution of oxygen, in the respiring liquid, is effected by maintaining gas (Oxygen) phase in contact with the liquid phase. In order to determine the oxygen demand, evolved carbon dioxide, due to biochemical activity, has to be absorbed from the gas phase and the change in pressure or volume provides an estimate of the oxygen consumed.

The disadvantage of such construction is that the instruments are elaborate and, further, means must be provided for causing an agitation of the complete instrument.

Since the apparatus is partially filled and closed, another disadvantage is that of leakages from the reaction vessel.

A further disadvantage is that such a respirometer is not suitable for routine work.

Yet another disadvantage is that evolved carbon dioxide has to be absorbed thereby raising the pH of the reaction mixture thus providing unnatural environmental conditions to the biomass in the respiring liquid.

OBJECTS OF THE INVENTION

A primary object of the present invention is to propose a respirometer for the study of BOD of less dilute wastewater samples that can be permitted in the standard BOD test procedure.

Another object of the invention is to propose a respirometer for testing of wastewater samples to determine its BOD and wherein the apparatus is not elaborate and hence suitable for routine testing.

Yet another object of the invention is to propose a respirometer for determining the BOD of wastewater samples and wherein, it is no longer necessary to absorb the evolved carbon dioxide thus providing natural environmental conditions to the bio-mass in the respiring liquid.

Yet another object of the invention is to propose a respirometer for testing of wastewater samples to determine its BOD and which also provides an indication of the instantaneous rate of BOD exertion.

SUMMARY OF THE INVENTION

It has now been found by the applicant that the limitations of the known respirometers can be obviated by interposing a non-porous film or membrane permeable to oxygen, between the respiring liquid and the gas phase. Absorption of oxygen now takes place from the gas phase to the non-porous film and then to the respiring liquid. Oxygen demand is estimated by determining dissolved oxygen in water. Hence evolved carbon dioxide need not be absorbed from the gas phase.

According to this invention, there is provided a respirometer for the determination of oxygen demand of a respiring liquid comprising a chamber wherein the walls of the said chamber are formed from a membrane permeable to oxygen but impermeable to water so as to allow diffusion of oxygen from the surrounding medium (gas phase) to the respiring liquid, thereby simultaneously replenishing, in part or full, the oxygen consumed in the respiring liquid. The said chamber of the present invention possesses means providing capability to the said chamber so that it can be used as a respirometer.

Applicant is briefly referring to the theory of the respirometer of the present invention, from which it will be apparent that the chamber or container structure of the present invention can be used as a respirometer and further that the BOD of less dilute samples can be determined in the respirometer of the present invention which could not readily be determined by prior art procedures.

When the respirometer is filled with the respiring liquid, processes of deoxygenation and reoxygenation take place simultaneously. The phenomenon of deoxygenation results from the consumption of dissolved oxygen on account of aerobic activity in the respiring liquid and reoxygenation replenishes, in part or full, the depleted oxygen in the respiring liquid. A high level of reoxygenation of a respirometer is thus required for the BOD determination of a concentrated wastewater sample having high concentration of oxygen consuming biodegradable organic matter. In the respirometer, the quantity of oxygen exchanged between the respiring liquid and the gas phase is determined by estimating the amount of oxygen added to the respiring liquid due to reoxygenation and which in turn provides an estimate of the BOD of the wastewater sample.

Rate of reoxygenation of the respirometer of the present invention is experimentally evaluated when the rate of deoxygenation of the contained respiring liquid is zero, e.g., when the respirometer is filled with distilled water from which dissolved oxygen has been removed. The experimental data is fitted to the appropriate mass (oxgyen) transfer model. Experimental data for the estimation of BOD of the wastewater sample is determined under essentially identical conditions under which the respirometer was standardised. The said conditions refer to the parameters of the said chamber and other environmental factors. The said parameters of the chamber are brought out with reference to the known mass(oxygen)transfer models.

The standardisation data of the respirometer is fitted to one or more of the oxygen (mass) transfer models depending on the conditions prevailing during the course of the experimental determination of the data. When liquid in the respirometer is stirred such that the thickness of the thin stagnant liquid film remains constant and there is no holdup of dissolved oxygen in the thin stagnant liquid film, the standardisation data is fitted to the film model, and, rate of oxygen transfer in the respirometer is given by:

$$dc/dt = K_L° a° (C_S - C) \qquad (1)$$

where dc/dt = rate of reoxygenation of the respiromer $K_L°$ = Overall oxygen transfer co-efficient.

a° = ratio of the area (A) of the membrane liquid interface per unit volumetric capacity (V) of the respirometer i.e. a° = A/V $C_S$ = Saturation dissolved oxygen concentration in the respirometer at test temperature and pressure.

c = dissolved oxygen concentration in the respirometer at test temperature and pressure.

$C_S - c = D$, and D is termed as dissolved oxygen saturation deficit.

$K_L° a° = r$, and r is termed as the respirometer constant.

When the contents of the respirometer are not stirred concentration gradients exist in the bulk liquid phase. Membrane surrounding the liquid as well as bulk liquid phase offer resistance to mass transfer. Oxygen transfer in the respirometer is then modelled on the known "Penetration Model". Briefly it may be stated that due to absence of mixing and existence of concentration gradients and holdup of dissolved oxygen in liquid layers adjacent to the membrane, rate of oxygen transfer in the respirometer is controlled by depth of liquid along the diffusion path. Thus rate of oxygen transfer in the respirometer is controlled by liquid depth profiles of the respirometer viz. exact geometric shape and size of the respirometer in addition to other factors given by equation (1).

Thus referring to equation (1), the kinetic mode of the respirometer or rate of reoxygenation of the respirometer is determined by the respirometer constant, r $(=K_L° a°)$. To ensure reproducibility of the kinetic mode of the respirometer, reproducibility of respirometer constant, r, has been ensured for the chamber of the respirometer of the present invention. This is achieved by ensuring repeatability of overall mass transfer co-efficient and further also by ensuring reproducibility of the area to volume ratio a°. Repeatability of $K_L°$ is ensured firstly, by specifying the quality and thickness of the membrane to ensure a reproducible value of the permeability of oxygen of the membrane, and secondly by uniform rate of stirring when the contents of the respirometer are imparted a stirring action. Repeatability of the area to volume ratio a° as in equation (1) is ensured by the reproducibility of the geometric shape and size of the chamber of the respirometer and also by maintaining a constant and uniform rate of stirring to effect uniform surface renewal at the membrane liquid interface when the contents of the respirometer are imparted a stirring action. The geometric shape and size of the respirometer is charactersied as the geometric mode of the respirometer. Geometric mode of the respirometer is thus controlled by liquid depth profiles.

Reliability of the computed valve of BOD from the respirometer data is ensured by reproducing and maintaining the same kinetic mode or rate of reoxygenation of the respirometer during the course of BOD testing as initially determined experimentally. This is ensured by using same quality and thickness of the membrane as was used during standardisation. Further the same geometric mode of the respirometer is reproduced and maintained during the course of BOD testing as initially used during standardisation. In addition, the same geometric mode of the respirometer is maintained by preventing sagging of the membrane during the long course of the BOD testing. Reproducibility and maintainability of the geometric mode of the respirometer is ensured by suitable construction of the chamber of the respirometer.

Reproducibility of the geometric mode, of the respirometer formed only from a thin membrane, is difficult to be achieved and maintained due to irregular random folds in the membrane and also due to sagging of the membrane when the said chamber is filled with a liquid.

Thus, the respirometer of the present invention is formed from a chamber or container structure comprising a framed structure. The thickness and stiffness of the members of the said framed structure is greater than that of the said membrane. The said framed structure comprises a plurality of fixed members securely held by one or more supports extending between the said fixed members. The said fixed members may be of any shape and size e.g., may comprise of a plate, dish, disc, sleeve or rod. The said chamber of the respirometer has an opening to communicate within the compartment of the chamber. The said opening may be formed in the said fixed members or by the said supports.

Depending on the shape of the said fixed members, the respirometer (chamber) may be constructed in many different and varied shapes. The membrane, that may be employed to form the walls of the respirometer, can be of low density polyethylene. The lower the density of polyethylene, the higher will be the permeability of oxygen through it. Similarly, the lesser the thickness of the membrane the higher shall be the rate of reoxygenation of the respirometer. In order to avoid the sagging of the wall of the respirometer during the course of BOD testing, a thickness of 0.5 mil or more (1 mil = 0.025 mm) of the membrane is preferred though not limited thereto. However, a membrane formed from polymers such as polyvinyl acetate, teflon, and hydrogenated polybutadiene are also suitable to form the walls of the respirometer. In every embodiment of the respirometer, the quality and thickness of the said membrane has to be specified to ensure reproducibility of the overall mass transfer co-efficient $K_L°$.

In the preferred mode of the respirometer, the walls of the respirometer are formed from a single membrane. However the said walls may be formed from a plurality of membranes having different characteristics of diffusion of oxygen. Said characterstics of diffusion of oxygen may be due to the quality of membrane or due to different thickness of the membrane. Quality of membrane refers to chemical composition and density of the polymer. Previous growth history of the crystallites in the polymer is important. One wall may be relatively impermeable to oxygen whereas the other wall may be permeable to oxygen. Similarly, no membrane is totally impermeable to water. However, a membrane having little permeability to water (as is the case with most polymeric membranes) may be employed to form the walls of said respirometer.

In one embodiment of a disposable respirometer, the said respirometer comprises a chamber, said chamber comprising a framed structure having a thickness and stiffness greater than that of membrane, said framed structure comprising a peripheral stiffening frame, said respirometer formed by heat sealing two sheets of said membrane to the periphery of the said stiffening frame, leaving a collapsible opening to communicate within the said chamber.

In this embodiment of the disposable respirometer, rate of reoxygenation of the respirometer has been maximised.

Thus, referring to equation (1), the rate of oxygen transfer or rate of reoxygenation in the respirometer can be increased, if the value of respirometer constant, r ($=K_L° a°$) is increased. Value of $K_L°$ is increased by suitable selection of membrane material having high permeability to oxygen and also by using a membrane of lesser thickness. Further, r can be increased by increasing area to volume ratio $a° (=A/V)$ which can be achieved by decreasing the volumetric capacity (V) of the respirometer for a particular membrane liquid interface area (A). Further, the value of r can be increased by increasing the membrane liquid interface area (A) for a particular volumetric capacity (V) of the respirometer.

The present invention is the first to increase $a°(=A/V)$ through decreasing volumetric capacity (V) of the respirometer for a particular membrane liquid interface area (A). This is achieved through the respirometer of the present invention which incorporates a peripheral stiffening frame to the chamber of the respirometer. The function of the peripheral stiffening frame in this particular construction of the respirometer is illustrated with the following example:

EXAMPLE 1

If a pouch is formed from two co-extensive sheets of a film sealed along the periphery leaving an opening and the said pouch (comprising a chamber to contain the liquid) is filled with water, it will inflate till it contains maximum amount of water and has a minimum area to volume ratio a°. When the said pouch is being filled with water, the co-extensive sheets move away from each other and the periphery of the pouch moves inward. In addition, irregular random folding of the edges of the pouch takes place. However, if the inward movement of the periphery of the pouch is restricted by a peripheral stiffening frame having much more stiffness than the stiffness of the film, the movement of the two co-extensive sheets away from each other shall be comparatively lesser. Incorporating the said peripheral stiffening frame to the said pouch, thus decreases its volumetric capacity for the same area of the co-extensive sheets, thereby increasing the area to volume ratio (a°) and increasing the respirometer constant, r, and from equation (1), increasing the rate of reoxygenation of the respirometer if the said film is permeable to oxygen.

Thus, a substantially high rate of reoxygenation of the contained sample is effected by incorporating the said peripheral stiffening frame in the pouch of the present invention. The said increase in rate of reoxygenation is effected through a particular construction of the respirometer. However, the rate of reoxygenation can be further increased (over and above the previous increased rate effected due to peripheral stiffening frame) by imparting a stirring action to the contained liquid sample. Thus the BOD of concentrated (less dilute) samples can be evaluated in the respirometer of the present invention, further with and without imparting a stirring action to the contained wastewater sample. This makes it possible to study the effect of stirring on the course of BOD exertion in the less dilute environment.

The increase in area to volume ratio of the respirometer, incorporating the said peripheral stiffening frame, depends on the stiffness of the said frame. A preferred mode of fabrication of the respirometer is to seal two co-extensive sheets of the said membrane to the periphery of the said frame. However sealing of co-extensive sheets is not critical since the same increase in area to volume ratio may be achieved by sealing said sheets a little loose on the periphery of a comparatively more stiffer frame.

Referring to example 1, without the peripheral stiffening frame, the periphery of the pouch would move inward, creating irregular random folds along the edges of the pouch resulting in localised pockets of liquid volume from where irregular exchange of fluid would occur even if rate of stirring is uniform thus resulting in variations in thickness of the stagnant liquid film and repeatability of $K_L°$ would not be ensured.

Further, wide variations in area to volume ratio (a°) would occur due to irregular random folding of the edges of the pouch without the feature of a stiff peripheral frame. With the peripheral stiffening frame, the said respirometer has well defined boundries of the membrane and allows the respirometer to have well defined and reproducible liquid depth profiles when filled with the liquid sample, thus ensuring reproducibility of the geometric mode of the respirometer.

Dissolved oxygen may be determined in the contained sample by inserting a dissolved oxygen probe from the said opening of the respirometer. Dissolved oxygen may also be determined by siphoning out the contained sample and then performing chemical estimation by the more accurate 'Winkler Method'.

The peripheral stiffening frame and the co-extensive sheets of the respirometer of the present invention keep the said sheets in tension when the said respirometer is full with the liquid sample. When the sample is being siphoned out, tension on the said sheets is released, the said stiffening frame pulls the said sheets to their original position and the contained sample is siphoned out without bringing in air in the chamber of the respirometer. Thus the co-extensive sheets are only critical when the liquid sample is to be siphoned for dissolved oxygen determination. When dissolved oxygen is determined by inserting dissolved oxygen probe. A respirometer with co-extensive sheets is not critical. Similarly incorporation of the said collapsible mouth in the respirometer is not critical when dissolved oxygen is determined by inserting and keeping the dissolved oxygen probe in the said opening of the respirometer.

During the long course of BOD testing, the said stiffening frame prevents sagging of the walls of the respirometer since the weight of water is uniformly distributed and borne by the said stiffening frame.

Thus, the said peripheral stiffening frame in the respirometer of the present invention ensures reproducibility of the overall mass transfer co-efficient $K_L°$ and prevents distortion of said pouch and ensures reproducibility of the geometric mode of the respirometer (by ensuring reproducibility of liquid depth profile) and hence ensures reproducibility of the rate of reoxygenation or kinetic mode of the respirometer providing accurate standardisation.

Further, the said peripheral stiffening frame maintains the said geometric mode of the respirometer (by preventing sagging of the walls) during the long course of BOD testing and hence ensures reliability of the computed values of the BOD from the respirometer data.

In the peripheral stiffening frame, the said fixed members were formed integral with the said supports forming the said framed structure of the respirometer. In another embodiment of the respirometer, the said fixed members are formed from plates. Thus, the chamber of the respirometer is formed of a base plate or a dish and a cover plate or a dish separated and securely held by one or more supports extending between the said base and cover plate. The cover plate has an opening for the introduction of a dissolved oxygen probe. The cover plate has a fixed collar for storing a liquid under test such as water or wastewater samples. The cover and base plates are each slightly tapered and, preferably, in a direction opposite to each other. The base plate and cover plate are provided each with a groove for accommodation of an O-ring. The membrane forming the walls of the respirometer, is in the form of an annular membrane. The said respirometer is formed by holding the lower end of the said membrane to the said base plate with a collar complementary to it whereas the upper end of the said membrane is held to the said cover plate with a collar complementary to it. The BOD of the wastewater sample may be determined with or without imparting a stirring action to the contained sample. By imparting stirring action to the contained sample, effective membrane liquid interfacial area is increased, thereby increasing the rate of reoxygenation of the respirometer and BOD of comparatively less dilute samples can be determined with stirring of the sample. Stirring of the contained liquid in the respirometer is caused by a rotor, placed in a depression in the base plate, said rotor is rotated by a magnetic stirrer, known as such in the art.

In this embodiment of the respirometer, said cover plate has second and third opening for inlet and outlet for said sample and said respirometer to be used for continuous flow system, e.g., modeling of complete mixed aerated lagoon.

In this embodiment of the respirometer, experimental errors are minimised by suitable container construction and by preventing leakages.

The joint of dissolved oxygen probe, with the cover plate is made air tight and closed to the atmospheric air. Further, by providing a fixed collar on the said cover plate, and storing the liquid under test, I prevent any leakage of gas or vapours through the said joints. Further, joints of membrane with the base and cover plates, are made air tight. The lower end of the membrane is held tightly between the base plate and its complementary collar. Similarly the upper end of the membrane is held tightly inbetween the cover plate and its complementary collar. Further rubber O-rings are inserted in grooves in the said base and cover plates and said O-rings are kept slightly projecting outward. Thus, the respirometer is closed to the atmospheric air except through the said membrane.

Reproducibility of the geometric mode of the respirometer is ensured by the said framed structure of the respirometer formed by the base plate, cover plate and the support or supports extending inbetween the plates. Further, the said annular membrane is tightly held over the base and cover plate by the respective complementary collars. Further, slightly projecting O-rings and taper on the said plates help in keeping the said membrane in one fixed position. The said support or supports extending between the said base and cover plates prevent relative movement of said base and cover plates, thereby preventing folding of the membrane and ensure reproducibility of the geometric mode of the respirometer. Further, the weight of water is borne by the base plate and the membrane is subjected to internal water pressure putting it under tension. This helps in preserving the fixed geometric mode of the respirometer during the long course of BOD testing and thus ensures reliability in the computed values of BOD from the respirometer data.

In the preferred mode of application of this respirometer the contained sample is provided a uniform stirring action by the said rotor. The said rotor is placed in a central depression on the inner surface of the said base plate which provides a guided movement to the said rotor and prevents its displacement towards the edges of the said base plate. This helps in keeping the thickness of thin stagnant liquid film constant ensuring reproducibility of $K_L°$ and uniform surface renewal at the membrane liquid interface. This ensures reproducibility of the rate of reoxygenation of the respirometer.

This embodiment of the respirometer may be adopted for the BOD study of continuous flow systems, which is achieved by providing holes for the inlet and outlet of the wastewater sample. These holes may be provided in the said cover and base plates.

When the diameter of the said annular membrane is small (say 1.5 cm or less) and a hole is provided in each of said cover and base plates, the said fixed members are formed from sleeves or rings instead of plates. In such an embodiment of the respirometer, there is one inlet and one outlet sleeve. Said sleeves are supported by one or more supports extending between the said sleeves. The said annular membrane is slipped over the said sleeves with complementary collars. The said sleeves are provided with a T-joint or Y-joint at each of the opening in the sleeves. One opening of each T-joint is used for the introduction of a dissolved oxygen probe at the inlet and the outlet. The remaining opening of each T-joint serves as an inlet and outlet for the wastewater sample. Thus one or more number of said respirometers may be used for the study of BOD of wastewater in continuous flow systems. When the diameter of the annular membrane is more, the said membrane may be strengthened with more supports integral with the said membrane. This will prevent sagging of the membrane during the course of BOD testing.

This embodiment of the respirometer, without the said T-joints, may be formed to serve as a disposable respirometer. Such an embodiment of the respirometer is formed by a top and a bottom sleeve and by one or more supports extending between the said sleeves. The said annular membrane is sealed onto said sleeves. The said supports may or may not be sealed onto said annular membrane. The bottom sleeve end of the respirometer is closed, e.g., by sealing the membrane and the top sleeve end is slipped over the dissolved oxygen probe and tightly held in position. In such an embodiment of the disposable respirometer, the weight of contained liquid is borne by the said membrane at the closed end and then transferred to the bottom sleeve and then to the top sleeve through the said supports. Such an embodiment of the disposable respirometer is suitable up to a limited volumetric capacity. Depending on the thickness of membrane used in the fabrication of the respirometer, this embodiment of the respirometer is suitable up to 125 ml volumetric capacity of the respirometer. Volumetric capacity of the respirometer is the total volume of liquid contained in the chamber of the respirometer with the said dissolved oxygen probe inserted in it.

In the preferred mode of the respirometer, said sleeves are at the extremities of the said supports. However, said supports may project out of the sleeves or rings for better grip to the dissolved oxygen probe.

In another embodiment of the respirometer, the bottom sleeve, as in the last embodiment of the respirometer, is also dispensed with. The said framed structure comprises of a plurality of rods or sticks securely held by supports between the said sticks, and said supports forming a sleeve. The respirometer is formed by sealing the said annular membrane onto the said sticks and said sleeve (formed from supports). The lower end of the said annular membrane is closed, e.g., by heat sealing the membrane. The sleeve is slipped over the dissolved oxygen probe and tightly held in position. In such an embodiment of the disposable respirometer, the weight of contained liquid is borne by the said membrane at the closed end and then transferred to said sleeve through the said rods. Depending on the thickness of the membrane used in the fabrication of the respirometer, this embodiment of the respirometer is suitable up to 75 ml volumetric capacity of the respirometer. Volumetric capacity of the respirometer is the total volume of liquid contained in the chamber of the respirometer with the said dissolved oxygen probe inserted in it. Irregular random folding of the membrane at the said closed end is restricted since the boundries of the membrane are fixed by said sticks and the membrane is subjected to little tension due to the weight of water.

In the preferred mode of the respirometer, said supports in the form of said sleeve are at one extremity of said sticks. However said sticks may project out of the sleeve for better grip to dissolved oxygen probe.

From the respirometer data, the BOD of the wastewater sample is computed by the numerical integration of the basic differential equation of the 'sag curve' known in the art and which may be written as:

$$\pm \Delta D + \overline{rD} \Delta t = \Delta Y \quad (2)$$

where
  $D = C_s - c$ as in equation (1)
  $r = K_L^\circ a^\circ$ as in equation (1)
  $\Delta D$ respresents the change in saturation deficit due to combined effects of reoxygenation and deoxygenation in the respirometer.
  $\overline{D}$ = average saturation deficit over the interval $\Delta t$.
  $\Delta Y$ = BOD of the wastewater sample over the time interval $\Delta t$.

Thus instantaneous rate of deoxygenation ($\Delta Y/\Delta t$) may also be estimated from the respirometer data.

SCOPE OF THE INVENTION

According to this invention, there are provided various embodiments of the respirometer for testing the biochemical oxygen demand of a wastewater sample. The walls of the various embodiments of the respirometer are formed from a membrane which is permeable to oxygen, thus allowing reoxygenation of the contained sample. The membrane is impermeable to water to enable it to store and retain the contained sample, such as a wastewater sample.

The chamber of various embodiments of the respirometer is designed, so that the said chamber can be used as a respirometer. To achieve this and to conform to the laws of mass transfer, the said chamber ensures reproducibility of the geometric mode (geometric shape and size) of the respirometer. Further, the said chamber prevents irregular random folding of the membrane and further, said chamber of the various embodiments of the respirometer maintains the same geometric mode during the long course of BOD testing.

The said chambers are formed from a framed structure. The thickness and stiffness of individual members of the said framed structure is much more than that of membrane. The said framed structure is formed from a plurality of fixed members securely held by one or more supports extending inbetween the said fixed members. Said supports may be formed from straight or curved members. The membrane is securely held onto said fixed members. The said support may or may not be integral with the said fixed members. The said membrane may or may not be securely held onto said supports. The said fixed members may be formed from a plate, dish, sleeve ring or rod. Depending on the shape of said fixed members and supports, the respirometer of the present invention may be fabricated in various shapes (embodiments).

In one embodiment of a respirometer, said framed structure comprises of a peripheral stiffening frame. The said fixed members are formed of strips of plates and are integral with the said supports. In another embodiment of the respirometer, said framed structure comprises of a base plate and a cover plate securely held by one or more supports extending between the said plates. The said fixed members are formed of plates. In still another embodiment of the respirometer, the said framed structure is formed from inlet and outlet sleeves securely held by one or more supports extending inbetween the sleeves. Said fixed members are formed of sleeves. In still another embodiment of the respirometer the said framed structure is formed from top and bottom sleeves or rings securely held by one or more supports extending between said supports. Said fixed members formed by sleeves or rings. In yet another embodiment of the respirometer, the said framed structure is formed from a plurality of rods or sticks securely held by supports extending between the said rods and the said supports forming a sleeve on one extremity of the rods. Said fixed members are formed of rods. All joints are air tight. In these embodiments of the respirometer, it is critical to securely hold the said membrane on the said fixed members. The various embodiments of the respirometer incorporate reoxygenation of the contained sample. Said embodiments of the respirometer incorporate a framed structure which is in the form of a peripheral stiffening frame in the said pouch. In another embodiment, it is formed from base and cover plates alongwith one or more supports and in another embodiment, it is formed from sleeves alongwith one or more supports and yet in another embodiment it is formed from sticks and a sleeve acting as a supporting member. Said framed structure, in various forms, prevents distortion of the chamber of the respirometer, thus ensuring reproducibility of the geometric mode of the respirometer and further, said framed structure maintains the said geometric mode of the respirometer during the course of testing ensuring reliability in the computed value of BOD.

The respirometer may be used with or without imparting a stirring action to the contained sample. Stirring of the contained sample may be carried out by a suspended stirring leg that is suspended alongwith the said dissolved oxygen probe. The said membrane is securely held to the members of said framed structure by heat sealing or sealing with an adhesive known as such in the art. The said membrane may also be securely held by removable collars forming air tight joints. Said dissolved oxygen probes form air tight joints with the holes provided in the various embodiments of the respirometer.

The term reproducibility refers to statistical limits in variation of the said data. Limits in variations of the data depend on the design of the apparatus and the technique and care of the analyst. The extent of limits of variations to be provided in a particular experimental set up depend on user acceptability. The embodiments of the respirometer, of the present invention, are suitably designed to prevent irregular random folding of the membrane of the said respirometer but the same may not be achieved in 100% of the cases. Irregular random folding of the membrane of the respirometer is bound to occur within limits depending on the technique and care of the analyst. The design of the various embodiments of the respirometer coupled with careful use of the said respirometer by a trained analyst ensures reproducibility of the respirometer constant of the said respirometer irrespective of whether irregular random folding of the membrane of the said respirometer occurs within the statistical limits of variation or not.

To ensure accuracy of the computed values of BOD from the respirometer data, a co-efficient of variation '$C_v$' of the respirometer constant of the said respirometer is kept within 5% of the average and the said reproducibility of the respirometer constant may be achieved by careful use of the respirometer by a trained analyst.

The term gas phase refers to any medium (phase) containing oxygen, e.g., air, pure oxygen or water containing dissolved oxygen. The preferred mode of the gas phase is the atmospheric air.

The preferred mode of application of the respirometer is as a completely filled vessel closed to the gas phase except through the membrane. However the said embodiments of the respirometer can be used as partially filled and open to the gas phase. In such an instance, the dissolved oxygen concentration is to be determined at a number of locations and also the application of the mass transfer model is not convenient. Such an experimental configuration is inconvenient to the analyst.

Applicant fabricated respirometers with different values of respirometer constants. A rough idea of the reproducibility of the respirometer constant may be had from the co-efficient of correlation of the data. Observed variations in co-efficient of correlation were from 0.96 to 0.99. Respirometers having different values of respirometer constants may be used for different concentrations of wastewater as illustrated in Table: I.

TABLE I

| Respirometer Constant ($h^{-1}$) | Ultimate BOD of standard wastewater (mg/l) |
|---|---|
| 0.50 | 50 |

TABLE I-continued

| Respirometer Constant ($h^{-1}$) | Ultimate BOD of standard wastewater (mg/l) |
|---|---|
| 0.75 | 100 |
| 1.50 | 200 |
| 2.00 | 300 |

Standard wastewater is prepared by adding equal amounts of glucose and glutamic acid plus nutrients as is known in the art.

PREFERRED APPLICATION OF VARIOUS EMBODIMENTS

Various embodiments of the respirometer may be used for different uses of oxygen demand determination in the area of water pollution control. In the preferred application, said respirometer in the form of the pouch may be used for raw wastes having high BOD values. Said respirometer comprising of base plate and cover plate may be used for routine use. These respirometers, employing a plurality of membranes having different characteristics of diffusion of oxygen may be used for modeling deoxygenation in large bodies of water. A respirometer with inlet and outlet sleeve may be employed for 'online' study of BOD of a wastewater. The respirometer with top and bottom sleeves and the said respirometer with the sticks and a sleeve may be usefully employed for BOD determination of treatment plant effluents.

In any embodiment of the respirometer BOD may be determined with or without imparting stirring action to the said sample. Depending on the intensity of stirring, a 300% increase in rate of reoxygenation of the respirometer may be obtained by stirring the sample.

By suitable selection of membrane material, embodiment of the respirometer and rate of stirring, respirometers, having a value of respirometer constant more than 2.0 may also be fabricated.

BRIEF DESCRIPTION OF THE DRAWINGS

This invention is more particularly described with reference to the following drawings, in which.

PREFERRED EMBODIMENT OF THE INVENTION AND DETAILED DESCRIPTION OF THE DRAWINGS

The membrane or sheet that may be employed to form the walls of the respirometer can consist of low density polyethylene. The lower the density of polyethylene, the higher will be the permeability of oxygen through it. Similarly, the lesser the thickness of the membrane, the higher will be the rate of reoxygenation of the respirometer.

Figure 1:
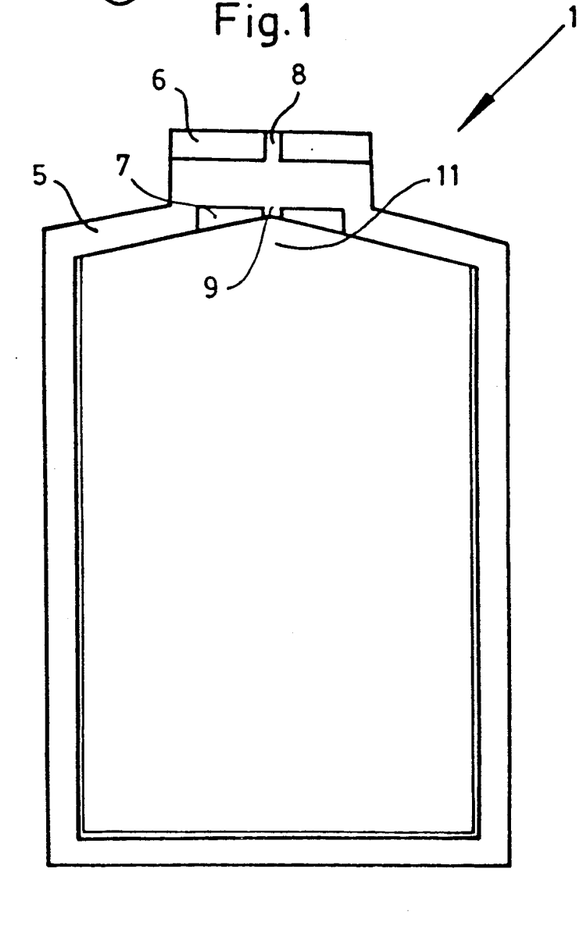
FIG. 1 is an elevational view of the respirometer in accordance with one embodiment of the present invention.
Figure 2:
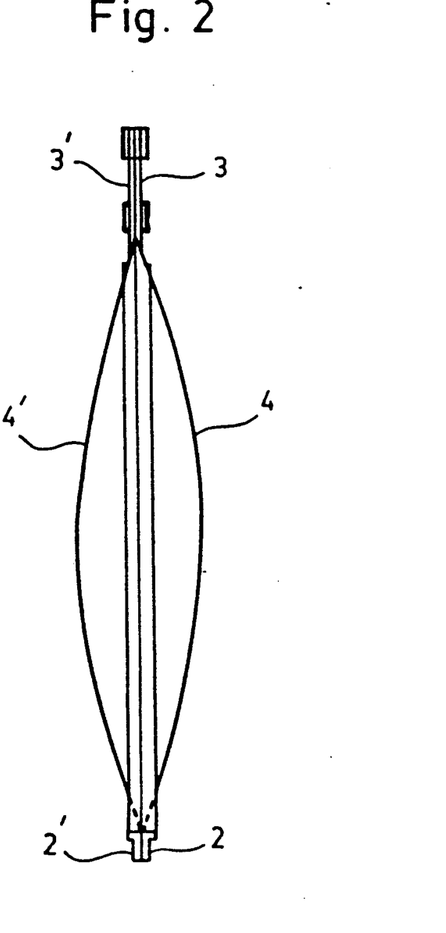
FIG. 2 is a side view of the respirometer of FIG. 1 and the liquid sample contained therein.
Figure 3:
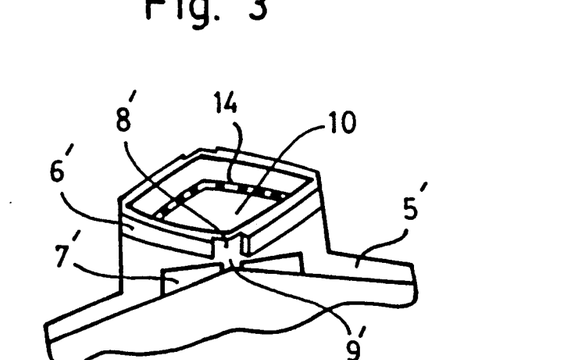
FIG. 3 is an isometric view of the collapsible mouth in open position.
Figure 5:
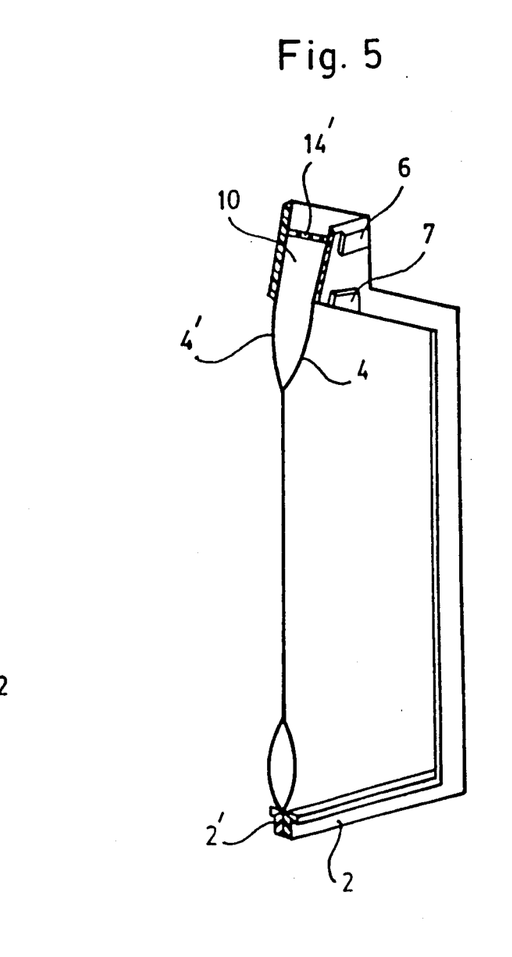
FIG. 5 is an isometric view of section at I—I of the respirometer of FIG. 4 with the sample contained therein and the collapsible mouth in open position.

The respirometer 1 (FIG. 1) comprises a stiffening frame and consists of a back frame 2' and a front frame 2. Two sheets 4 and 4' of said membrane are sandwiched between the front frame 2 and back frame 2'. The periphery of the said frames 2 and 2' alongwith said sheets 4 and 4' are heat sealed to each other along the periphery except at the collars 3 and 3' so that the said sheets 4 and 4' are coextensive to the stiffening frame as shown in FIG. 1. Collapsible mouth 10 is formed by heat sealing the said sheets 4 and 4' along the seams 14 and 14' on the collars 3 and 3' of front and back frames 2 and 2' as shown in FIGS. 3 and 5. A gullet 11 is formed by the upper raised portions 5 and 5' of frames 2 and 2' alongwith the said sheets 4 and 4'. The said stiffening frame is made of low density polyethylene, so as, to heat seal the low density polyethylene sheets 4 and 4' with it. The thickness of frame 2 may be 1 mm or more. The thickness of collar 3 is 1 mm or more except at the reinforcing ribs 6 and 7 where the thickness has been increased to 2 to 4 mm. Vertical slits 8 and 9 are formed in the reinforcing ribs 6 and 7 respectively, where, the thickness has been reduced to 1 mm. The collapsible mouth 10 is opened by pressing its sides with the thumb and forefinger of the hand. The vertical slits or cuts 8 and 8', 9 and 9' facilitate an easy opening of the said mouth 10 as shown in FIGS. 3 and 5. When the collars 3 and 3' are pressed against each other, the collapsible mouth 10 is in the closed position and the ribs 6, 7 and 6', 7' of collars 3 and 3' help in keeping the said mouth 10 in the closed position due to their increased thickness and stiffness.

Figure 4:
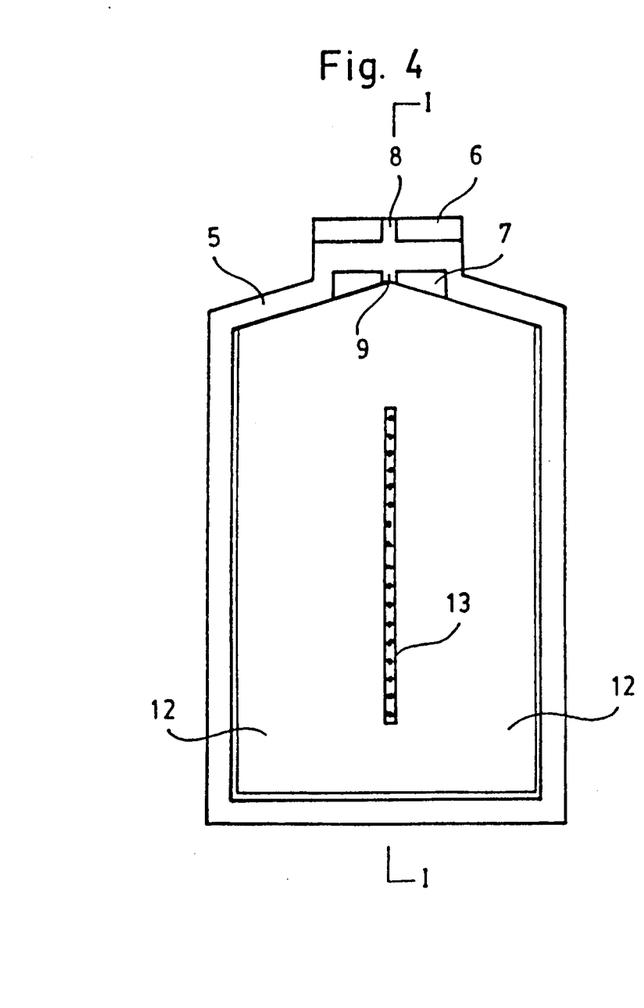
FIG. 4 is an elevational view of the respirometer in accordance with another embodiment of the respirometer of FIG. 1.

In accordance with another embodiment of the present invention of FIG. 1, and, as shown in FIGS. 4 and 5, the respirometer has a plurality of interconnected vertical compartments 12 of equal width. The interconnected vertical compartments 12 of equal width are formed by heat sealing the said sheets 4 and 4' along the vertical seam 13 as shown in FIG. 4. Due to the vertical seam 13, the movement of the two sheets 4 and 4' away from each other is prevented when the respirometer is filled with the liquid sample. Due to vertical seam 13 the volumetric capacity of respirometer gets further reduced and is lesser than that of the respirometer without said vertical seam. Thus, the area to volume ratio of the respirometer having interconnected equal width compartments formed by one or more vertical seams 13 gets further increased in comparison to that of a respirometer having only a single compartment. Thus, the rate of reoxygenation of the contained sample in the said respirometer with vertical seam or seams, gets further increased over and above the high level of reoxygenation in the respirometer having a single compartment.

Applicant observed that by providing said stiffening frame in the respirometer, the increase in area to volume ratio is between 70 to 150% more than that of a respirometer without the said stiffening frame.

In operation, the wastewater sample is filled into the respirometer up to gullet 11 so as to completely expel air from the respirometer. Thereafter, mouth 10 of the respirometer is closed and gripped with a paper clip and hung in an incubator having a fixed test temperature. Alternatively, a dissolved oxygen probe is introduced into the said mouth 10 which is so sized. Thereafter the respirometer is clamped in a stand and placed in the said incubator.

A comparison of the respirometers with and without the stiffening frame was made. The said respirometers were standardised and respirometer constants estimated by regression analysis. Respirometers with a stiffening frame gave a substantially better co-efficient of correlation (0.97 to 0.99) in comparison to respirometers without the said stiffening frame (co-efficient of correlation 0.8 to 0.9), thus, indicating reliable and accurate standardisation of the respirometer with said stiffening frame.

In another embodiment of the respirometer, the respirometer frame comprising of base and cover plates and supports are to be formed from a material that is resistant to chemical and biological attack, e.g., glass, lucite glass, polyethylene and stainless steel. The complementary collars may be formed from rubber, fibre plastic and polyethylene.

Figure 6:
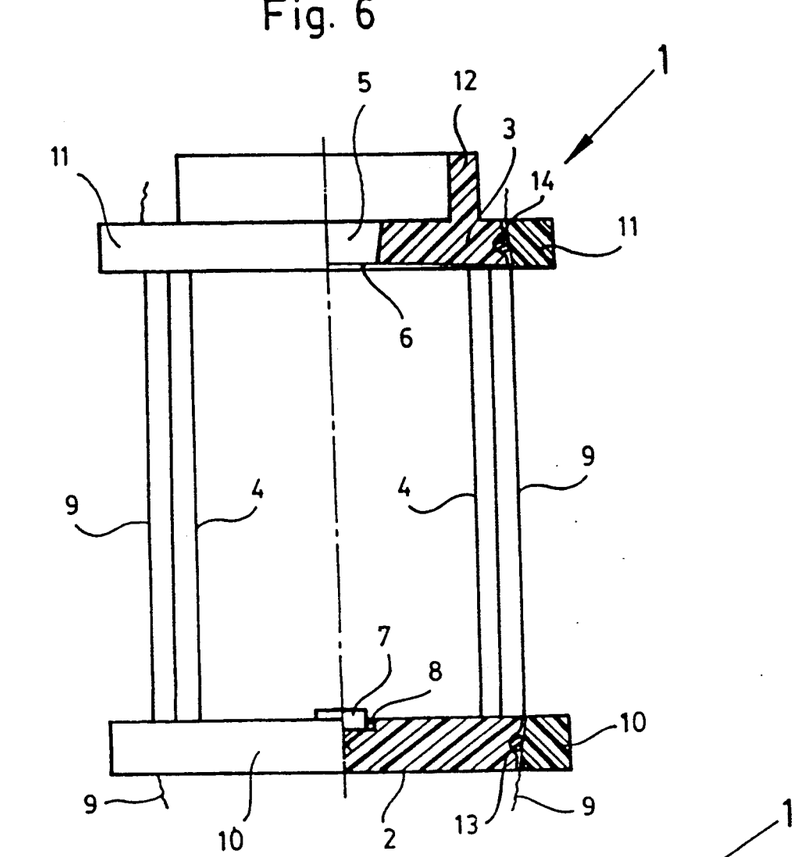
FIG. 6 is an elevational view of the respirometer in right half section in accordance with another embodiment of the present invention.

Referring to the drawing FIG. 6, the respirometer 1, of the present invention, comprises a chamber consisting of a base plate 2 and a cover plate 3 held together by means of a plurality of supports 4 extending between the said cover plate 3 and said base plate 2. Cover plate 3 has an opening 5 for introduction of a dissolved oxygen probe. A rotor 7 is placed in a central depression 8 in the base plate 2. The rotor is rotated by moving a magnet from under the base plate 2. The movement of the magnet and that of rotor 7 is caused by a magnetic stirrer known as such in the art. The speed of magnetic stirrer is kept constant during the course of standardisation and the same speed of the stirrer is maintained during the course of BOD testing. The central depression 8 in base plate 2 retains rotor 7 therein and, thus, preventing any drift or displacement of said rotor. It has been found that by providing base plate 2, rotor 7 moves on said base plate 2, and not on the membrane as in the instance when the entire chamber is fabricated from the membrane. In such an instance and during the testing period, the characteristics of the membrane will change due to movement of the rotor on the said membrane and also occassionally the membrane may even rapture, thus, spoiling the entire experimental set up. Alternatively, rotor 7 may be suspended alongwith the dissolved oxygen probe through hole 5 as is known in the art. In such an instance the size of base plate 2 may be reduced.

The chamber is formed preferably by the annular membrane 9 forming the wall surface of the respirometer. The lower end and the upper end of membrane 9 are held onto the base and cover plates 2 and 3 by the complementary collars 10 and 11 respectively. Membrane 9 is formed from any suitable material permeable to oxygen so that absorption of oxygen, present in atmospheric air, takes place at the said membrane surface. The absorbed oxygen further diffuses in the body of the membrane 9 and is then transferred to the waste-water sample contained within the chamber of the respirometer 1. The underside surface 6 shown in FIG. 6 of cover plate 3 is sloped upwards towards the centre to facilitate removal of entrapped air from the chamber since air bubbles rise up and are removed through the hole 5.

The chamber of respirometer 1 is closed to atmosphere except through membrane 9. This is achieved by providing sealing means at the various joints to prevent any exchange of gas or vapours from the chamber. One such sealing mean comprises of collar 12, on cover plate 3, to form storage means for storing a liquid under test such as water or wastewater sample. Further sealing means are provided on the joints, the lower end and upper end of membrane 9 with base plate 2 and cover plate 3, respectively. These sealing means comprise of rubber O-rings 13 and 14 provided in grooves on the circumference of base plate 2 and cover plate 3 respectively. The O-rings 13 and 14 are kept slightly projecting out from the grooves by about 0.5 to 1 mm. The peripheral side of the base plate 2 and cover plate 3 are slightly tapered. The lower end and upper end of annular membrane 9 are held tightly onto the circumference of base plate 2 and cover plate 3 by the respective complementary collars 10 and 11. The rubber O-rings 13 and 14 are compressed in the joints so formed, thereby making the joints leak proof and also air tight. Thus the chamber of respirometer 1 is closed to the atmosphere except through the membrane 9. Closing the chamber of the respirometer 1 to atmospheric air (except through the membrane 9) prevents introduction of unknown quantity of oxygen through uncontrolled sources, whereby, experimental errors are minimised. Tapered sides of base and cover plates 2 and 3 alongwith the O-rings 13 and 14 and the complementary collars 10 and 11 hold the lower end and upper end of annular membrane 9 tightly thus preventing its displacement during the period of testing. Alternatively the lower and the upper ends of membrane 9 may be sealed to base and cover plates 2 and 3 respectively. In such an instance, the respirometer may be disposed off after use.

In operation, the respirometer is standardised by the methods known in the art. Thus, the respirometer constant (r) is a known value for the respirometer for the specific thickness, quality of the membrane and under specified experimental conditions. For BOD determination of a wastewater sample, membrane 9 is changed for each test. Thus, annular membrane 9 is slipped over base plate 2 and cover plate 3. The lower end of the membrane is held tightly over the base plate 2 by the complementary collar 10. Wastewater sample is filled in the chamber and any entrapped air, in the chamber, is removed through the hole 5. Sloping underside 6 of cover plate 3 aids in easy removal of entrapped air bubbles. The upper end of membrane 9 is tightly held in hand and the complementary collar 11 slipped over cover plate 3. Wastewater sample completely fills the chamber but partially fills the collar 12. Dissolved oxygen probe is introduced into the opening 5. The respirometer 1 is then introduced into a constant temperature chamber and the contained liquid sample is stirred by the movements of 7 caused by a magnetic stirrer. The same speed of the magnetic stirrer is maintained as it was during the course of standardisation. The dissolved oxygen probe is connected to a meter or recorder giving reading of dissolved oxygen concentration (c) at zero time, and thereafter, at various intervals of time.

Figure 7:
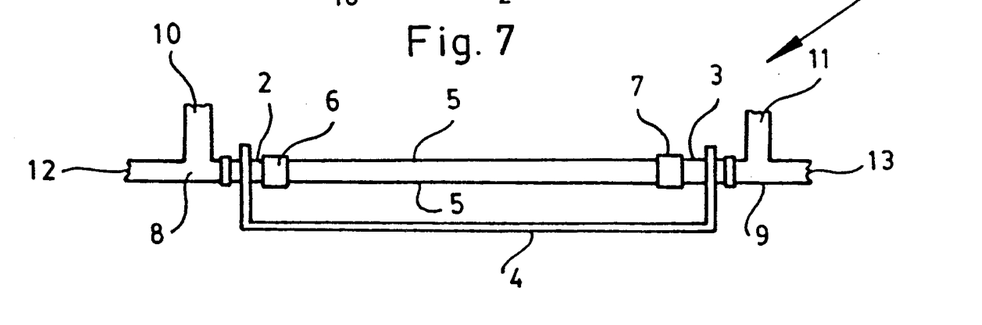
FIG. 7 is an elevational view of the respirometer in accordance with another embodiment of the present invention.

In accordance with another embodiment of the present invention and as shown in FIG. 7, the respirometer 1 is formed from inlet sleeve 2 and outlet sleeve 3 securely held by one or more supports 4 extending between the said sleeves 2 and 3. Annular membrane 5 is securely held onto said sleeves 2 and 3 by the respective collars 6 and 7. T-joints 8 and 9 are provided with each sleeve 2 and 3 in the openings 10 and 11, of T-joints 8 and 9, dissolved oxygen probes are inserted. The other openings 12 and 13, of respective T-joints 8 and 9, serve as inlet and outlet of sample for continuous flow systems.

Figure 8:
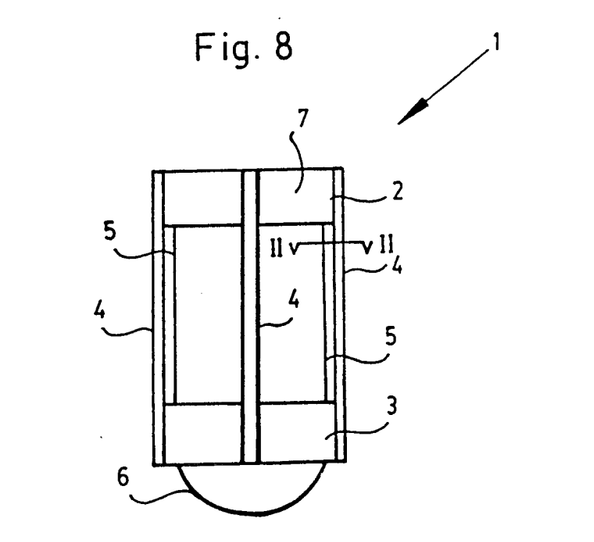
FIG. 8 is an elevational view of the respirometer in accordance with still another embodiment of the invention.
Figure 9:
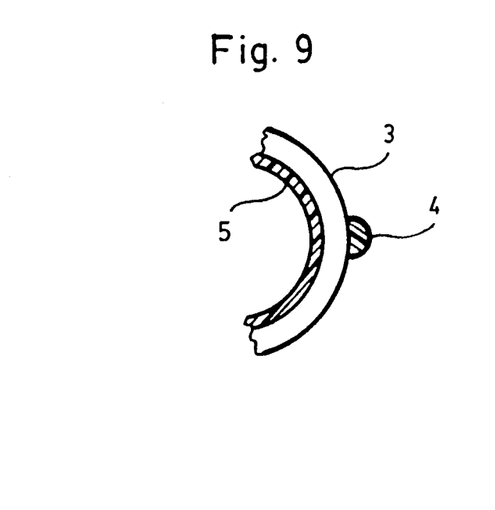
FIG. 9 is an enlarged sectional view of the respirometer of FIG. 8 with section at II—II.

In accordance with still another embodiment of the present invention and as shown in FIGS. 8 and 9 the respirometer 1 is formed from top sleeve 2 and bottom sleeve 3 securely held by one or more supports 4 extending inbetween the said sleeves 2 and 3. Annular membrane 5 is securely held onto said sleeves 2 and 3, e.g., by heat sealing. End 6 of the annular membrane 5 at the bottom sleeve 3 is closed, e.g., by heat sealing. Opening 7 at sleeve 2 is for introduction of a dissolved oxygen probe in air tight relationship.

Figure 10:
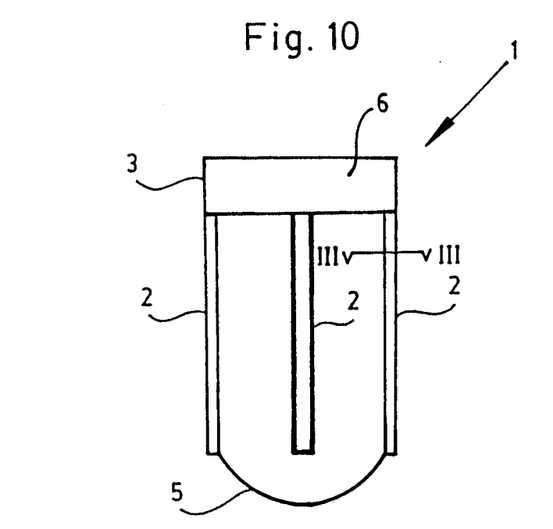
FIG. 10 is an elevational view of the respirometer in accordance with still another embodiment of the present invention.
Figure 11:
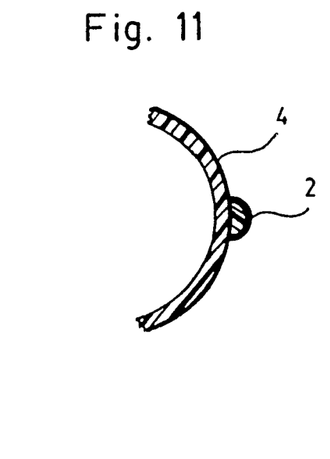
FIG. 11 is an enlarged sectional view of the respirometer of FIG. 10 with section at III—III.

In accordance with still another embodiment of the present invention, and, as shown in FIGS. 10 and 11, the respirometer 1 is formed by a plurality of the sticks or rods 2 securely held and supported by the sleeve 3 extending between the said sticks or rods 2. Annular membrane 4 is sealed onto said sticks or rods 2 and sleeve 3. End 5 of the annular membrane 4 is closed, e.g., by heat sealing. In the opening 6 at the sleeve end of the respirometer, a dissolved oxygen probe is inserted in air tight relationship.

In operation, said respirometer is filled with the sample and introduced in an incubator. Dissolved oxygen concentration of the said sample is noted at zero time and at intervals of time subsequently and BOD is calculated.

Thus taking into consideration that the respirometer constant, r, is a known value and knowing the value of average saturation deficit $\overline{D}$ at least for one interval of time, $\Delta t$, the amount of oxygen consumed $\Delta y$ in time interval $\Delta t$ can be evaluated from equation (2). Also $\Delta y / \Delta t$ gives the instantaneous rate of BOD exertion during the time interval $\Delta t$.

I claim:

1. A method of determining oxygen demand of a respiring liquid sample, comprising:
    (a) forming a respirometer housing having an opening for receiving the liquid sample and defining a liquid receiving cavity having a predetermined volume and a uniform cavity surface area;
    (b) forming at least a portion of the respirometer housing with a membrane wall permeable to oxygen, the membrane wall having a predetermined area;
    (c) estimating an oxygen transfer rate through the respirometer housing;
    (d) inputting the liquid sample into the cavity to form the predetermined volume and the uniform cavity surface area;
    (e) placing the housing with the respiring liquid sample therein in a gas phase environment containing oxygen;
    (f) thereafter determining the dissolved oxygen concentration of the respiring liquid sample; and
    (g) calculating the oxygen demand of the respiring liquid as a function of the estimated oxygen transfer rate and the determined dissolved oxygen concentration.

2. The method as defined in claim 1, wherein step (c) comprises:

forming a standardization housing for estimating the oxygen transfer rate through the respirometer housing, the standardization housing having a standardization liquid received cavity with the predetermined volume and uniform cavity surface area of the liquid housing, and having a standardization membrane wall area equal to the predetermined area of the membrane wall.

3. The method as defined in claim 2, wherein steps (b) and (c) further comprise:

forming the membrane wall having a predetermined thickness; and forming the standardization housing with a standardization membrane thickness equal to the predetermined thickness of a membrane wall.

4. The method as defined in claim 1, wherein step (d) further comprises:

removing air bubbles from the cavity prior to step (e) and subsequent to step (d), such that the respiring liquid sample occupies the entirety of the cavity.

5. The method as defined in claim 1, further comprising:

sealing the cavity with the liquid sample in the housing subsequent to step (d) and prior to step (e), such that substantially all gas passing into the cavity and from the cavity during step (e) passes through the membrane wall.

6. The method as defined in claim 1, further comprising:

monitoring the temperature of the respiring liquid during step (f).

7. The method as defined in claim 1, further comprising:

mixing the respiring liquid within the housing during step (f).

8. The method as defined in claim 1, further comprising:

replacing the membrane wall with another membrane wall;

sealing the another membrane wall to the remaining portion of the respirometer housing; and filling the respirometer housing having the another membrane wall with another liquid sample to determine the oxygen demand of the another respiring liquid sample.

9. The method as defined in claim 1, wherein step (e) comprises:

placing the housing within atmospheric air.

10. The method as defined in claim 1, wherein step (b) comprises:

forming a membrane wall from a low density polyethylene sheet material.

11. The method as defined in claim 1, wherein step (a) further comprises:

forming the respirometer housing with the opening being a fluid inlet for continuously passing liquid sample into the cavity, and forming the respirometer housing with a outlet for continuing passing the liquid sample out of the cavity.

12. The method as defined in claim 11, further comprising:

providing the housing with at least a pair of spaced sampling ports for determining the dissolved oxygen concentration during step (f).

13. A method of determining oxygen demand of a respiring liquid sample, comprising:

(a) forming a respirometer housing having an opening for receiving the liquid sample and defining a liquid receiving cavity having a predetermined volume and uniform cavity surface area;

(b) forming at least a portion of the respirometer housing with a membrane wall permeable to oxygen, the membrane wall having a predetermined area;

(c) estimating an oxygen transfer rate through the respirometer housing using a standardization housing with a standardization liquid receiving cavity having the predetermined volume and the uniform cavity surface area, the standardization housing having a standardization membrane wall area equal to the predetermined membrane wall area;

(d) filling the cavity with the liquid sample to form the predetermined volume and the uniform cavity surface area;

(e) sealing the cavity with the liquid sample therein such that substantially all gas entering and leaving the cavity must pass through the membrane wall;

(f) placing the sealed housing with the respiring liquid sample therein in a gas phase environment containing oxygen;

(g) thereafter determining the dissolved oxygen concentration of the respiring liquid sample as a function of time; and (h) calculating the oxygen demand of the respiring liquid sample as a function of the estimated oxygen transfer rate and the determined dissolved oxygen concentration.

14. The method as defined in claim 13, wherein steps (b) and (c) further comprise:

forming the membrane wall having a predetermined thickness; and forming the standardization housing with a standardization membrane thickness equal to the predetermined thickness of a membrane wall.

15. The method as defined in claim 13, wherein step (d) further comprises:

removing air bubbles from the cavity subsequent to step (d) and prior to step (e), such that the respiring liquid occupies the entirety of the cavity.

16. The method as defined in claim 13, further comprising:

monitoring the temperature of the respiring liquid during step (g).

17. The method as defined in claim 13, further comprising:

mixing the respiring liquid within the housing during step (g).

18. The method as defined in claim 13, further comprising:

replacing the membrane wall with another membrane wall;

sealing the another member wall to the remaining portion of the respirometer housing; and filling the respirometer housing having the another membrane wall with another liquid sample to determine the oxygen demand of the another liquid sample.

19. The method as defined in claim 13, wherein step (f) comprises:

placing the housing within atmospheric air.

20. The method as defined in claim 13, wherein step (b) comprises:

forming a membrane wall from a low density polyethylene sheet material.

* * * * *